United States Patent [19]

Jenkins et al.

[11] Patent Number: 4,940,587

[45] Date of Patent: Jul. 10, 1990

[54] ORAL PHARMACEUTICAL COMPOSITION THROUGH MUCOSA

[75] Inventors: Anthony W. Jenkins; Stewart T. Leslie, both of Cambridge, United Kingdom; Ronald B. Miller, Basel, Switzerland

[73] Assignee: Euroceltique, S.A., Luxembourg, Luxembourg

[21] Appl. No.: 870,027

[22] Filed: Jun. 3, 1986

[30] Foreign Application Priority Data

Jun. 11, 1985 [GB] United Kingdom ............... 8514665

[51] Int. Cl.$^5$ ........................... A61K 9/36; A61F 9/02
[52] U.S. Cl. ................................ 424/480; 424/434; 424/435; 424/436; 424/494; 424/495
[58] Field of Search .............. 424/422, 434, 435, 436, 424/468, 469, 480, 470, 476, 494, 495, 498

[56] References Cited

U.S. PATENT DOCUMENTS

| | | | |
|---|---|---|---|
| 3,916,899 | 11/1975 | Theeuwes et al. | 424/435 X |
| 4,039,653 | 8/1977 | DeFoney et al. | 424/435 |
| 4,226,848 | 10/1980 | Nagai et al. | 424/434 |
| 4,292,299 | 9/1981 | Suzuki et al. | 424/434 X |
| 4,572,832 | 2/1986 | Kigasawa et al. | 424/435 |
| 4,695,591 | 9/1987 | Hanna et al. | 424/436 |

FOREIGN PATENT DOCUMENTS 1171691 11/1969 United Kingdom ............... 424/435

Primary Examiner—Thurman K. Page
Attorney, Agent, or Firm—Steinberg & Raskin

[57] ABSTRACT

An arrangement is provided for the application of an oral pharmaceutical to the mucosa of the oral or nasal cavity, for sustained release there of the drug. The arrangement of the invention comprises a body which has a size and shape suitable for insertion into and retention in the oral or nasal cavity, the body being formed of granules of a higher aliphatic alcohol and a hydrated water soluble hydroxyalkyl cellulose having the drug distributed therethrough. This body is coated with a cellulose derivative which is adherent to the mucosa. As a consequence, upon insertion into the oral or nasal cavity, the body adheres to the mucosa and the drug is there slowly released and absorbed into the body. The arrangement is preferably in the form of a buccal tablet, particularly a kidney shaped buccal tablet. Any drug suitable for oral administration can be used, morphine being preferred. The cellulose derivative which is preferred is hydroxypropyl cellulose. The higher aliphatic alcohol is preferably cetostearyl alcohol, and the water soluble cellulose is preferably hydroxyethyl cellulose.

18 Claims, 3 Drawing Sheets

A. MORPHINE SULPHATE BUCCAL TABLET (20mg)
B. MORPHINE SULPHATE BUCCAL TABLET (10 mg)

ORAL PHARMACEUTICAL COMPOSITION THROUGH MUCOSA

BACKGROUND OF THE INVENTION

The administration of drugs using oral vehicles retained in the buccal cavity is known. Such administration is generally effected by inserting an oral vehicle (e.g. a tablet), containing a drug, into the buccal cavity of the patient's mouth and then passing the vehicle against the mucosa of the cheek or the gum until it adheres.

Absorption of the drug in the vehicle generally occurs directly through the mucosa at the inner surface of the cheek and/or gum into the patient's bloodstream. In some cases, however, the drug may be absorbed gastrically or enterally by the absorption of drug contained in swallowed saliva.

The buccal method of drug administration has considerable advantages over administration by, for example, swallowing a tablet or injection. One advantage is that administration can be discontinued at any time (e.g. when undesired effects arising from the administration are identified) simply by removing the remainder of the vehicle. Another advantage over oral administration, is that first pass drug metabolism may be avoided.

A particular problem associated with the buccal administration of drugs, however, is that the oral vehicle containing the drug tends, after a period of time, to become detached from the mucosa. At best this can be merely inconvenient, at worst it may lead to the patient swallowing the vehicle.

SUMMARY OF THE INVENTION

It is an object of the present invention to provide a sustained release, oral pharmaceutical composition having improved properties of adherence to mucosa within the oral or nasal, especially buccal cavity.

It is a further object of the present invention to provide an oral vehicle prepared from the improved composition and shaped to facilitate attachment within the buccal cavity.

With the above and other objects in view, the present invention mainly comprises an arrangement adapted for application and adherence to the mucosa of the oral or nasal cavity for sustained release there of an orally administerable drug, the arrangement comprising a body having a size and shape which is suitable for insertion into and retention in the oral or nasal cavity, the body being formed of granules of a higher aliphatic alcohol and a hydrated water soluble hydroxyalkyl cellulose having a drug distributed therethrough and being coated with a cellulose derivative which is adherent to the mucosa, whereby upon insertion into the oral or nasal cavity, the body adheres to the mucosa thereof and the drug is there slowly released and absorbed.

For facility of understanding the present invention, the coating of the cellulose derivative which is adherent to the mucosa will herein after being referred to as the "extragranular mucosa-adhesive cellulose". This extragranular coating is to be differentiated from intragranular cellulose which is distributed through the body but which may or may not provide sufficient surface coating for good adherence of the body to the mucosa.

Thus, the extragranular mucosa-adhesive cellulose of the present invention improves the attachment of the dosage form to the oral or nasal mucosa, especially within the buccal cavity.

Preferably the extragranular, mucosa-adhesive cellulose is applied to the granules in the form of a powdered solid rather than a solution. This allows greater control over the water content of the granules, avoids swelling of the granules and also avoids an unnecessary drying step.

It has surprisingly been found that by employing extragranular cellulose adhesive, especially powdered adhesive, the adherent properties of the resulting dosage form are significantly greater than those of a dosage form having intragranular adhesive only.

The mucosa adhesive cellulose may be, for example, a carboxyalkyl cellulose, such as sodium carboxymethyl cellulose or a hydroxyalkyl cellulose, such as hydroxypropylmethyl cellulose. Preferably, however, hydroxypropyl cellulose (HPC), especially that sold by the Hercules Powder Company as Klucel HF (Trade Mark), is the mucosa adhesive material.

Preferably, the mucosa adhesive cellulose is a high molecular weight material having a numerical average molecular weight above 200,000, especially above 500,000.

Surprisingly, when HPC is employed as the adhesive in the present formulation it is found to give the dosage form adhesive properties superior to those achieved using previously preferred adhesives, such as Karaya gum and acrylic acid polymers (e.g. carbopol gel) or mixtures of thse adhesives with other known binders.

The concentration of extragranular adhesive cellulose (as a proportion of the total dosage form weight) is preferably between 2% and 15% (w/w), especially between 4% and 10% (w/w).

Prior to compression, the granules coated with mucosa-adhesive cellulose will preferably have a granule size of less than 1000 μm.

The higher aliphatic alcohol is an aliphatic alcohol containing from 8 to 18 carbon atoms which is optionally substituted by a further aliphatic group containing from 8 to 18 carbon atoms. Suitable alcohols include lauryl alcohol, myristyl alcohol, stearyl alcohol, or, which is preferred, cetyl alcohol and cetostearyl alcohol. The higher aliphatic alcohol, together with the water soluble hydroxyalkyl cellulose, serves to control the release of the drug from the composition. The level of alcohol in the composition will therefore be determined by the rate of drug release required. Generally, however, the composition will contain between 5% and 35% (w/w), especially 10% and 30% (w/w), (as a proportion of the total dosage form weight) of the higher aliphatic alcohol.

The hydroxyalkyl cellulose is a hydroxy lower alkyl ether of cellulose and is preferably selected from the group consisting of hydroxymethyl, hydroxyethyl, hydroxypropyl and hydroxypropylmethyl cellulose, with hydroxyethyl cellulose (for example Natrosol 250 HX, Trade Mark, Hercules Powder Company) being particularly preferred. The hydroxyalkyl cellulose, together with the higher aliphatic alcohol, serves to control the release of the drug from the composition. The level of hydroxyalkyl cellulose in the composition will therefore be determined by the rate of drug release required. Preferably the composition will contain between 2% and 15% (w/w), as a proportion of the total dosage form weight, of the hydroxyalkyl cellulose.

It should be noted that when the water-soluble hydroxyalkyl cellulose used in the present composition is also the composition's mucosa adhesive, then the amount of hydroxyalkyl cellulose present in each dosage form is at least the sum of the hydroxyalkyl cellulose added as water-soluble hydroxyalkyl cellulose and hydroxyalkyl cellulose added as extragranular adhesive.

The drug employed in the present composition is preferably absorbable through the oral or nasal mucosa. In some instances, however, drugs that are absorbed gastrically and/or enterically (rather than via the mucosal route) may be employed. In a still further instance, the drug may be one that acts locally in the mouth, for example in the treatment of mouth ulcers. Suitable medicaments will be well known to those skilled in the pharmaceutical art. Listed below are certain of the drug categories within which are classed a number of the drugs that may be employed in the present composition.
(a) Analgesic agents; e.g. morphine, or analogues thereof, phenazocine, pentazocine, buprenorphine;
(b) Anti-inflammatory agents; e.g. ibuprofen, indomethacin, acetaminophen, phenacetin, aspirin, aminopyrine, sulpyrine, phenylbutazone, mefanamic acid, flufenamic acid, ibufenac, colchicine, probenecid, ethensamide, salicylamide, ketoprofen, flurbiprofen, diclofenac, clidana, alclofenac, sulindac, piroxicam;
(c) Antihistamines, e.g. clemastine fumarate, mepyramine, diphenylhydramine hydrochloride, dexchlorpheniramine maleate;
(d) Topical anaesthetics, e.g. benzocaine, procaine, lidocaine,
(e) Vasodilators, e.g. nitroglycerin, nifedipine, papaverine, isosorbide dinitrate, diltiazem, nicardipine;
(f) Antitussives and expectorants, such as codeine phosphate and isoproterenol hydrochloride;
(g) Hormones; e.g. insulin, vasopressin and heparin;
(h) Diuretics, e.g. ethacrynic acid and bendrofluazide;
(i) Anti/hypotensives, e.g. propranolal and clonidine;
(j) Anti-neoplastic agents, e.g. cytarabine and doxorubicine;
(k) Antidiabetic drugs, e.g. chlorpropamide and glibenclamide;
(l) Bronchodilators, such as albuterol (salbutamol), ipratropiumbromide;
(m) Antiarrythmic agents, e.g. verapamil;
(n) Anti-inflammatory steroids, e.g. hydrocortisone, prednisone, prednisolone, triamcinolone, dexamethasone, betamethasone;
(o) Antibiotics or Fungicides, e.g. tetracyclines, leucomycines, fradiomycins, penicillins, cephalosporins, erythromycins;
(p) Chemotherapeutic agents, e.g. sulphathiazole, nitrofurazone, clotrimazole;
(q) Cardiac tonics, e.g. digitalis, digoxin;
(r) Oral antiseptics, e.g. chlorhexidine, hexylresorcinol, dequalinium chloride and ethacridine;
(s) Antiasthmatics, e.g. disodium cromoglycate;
(t) Drugs acting on the central nervous system, e.g. diazepam and estazolam;
(u) Anti-epileptics, e.g. phenytoin, meprobamate and nitrazepam;
(v) Anticholinergics, e.g. scopolamine;
(w) Muscle Relaxants e.g. baclofen, dentrolene, sodium, cyclobenzaprine hydrochloride;
(x) Beta-blocker, e.g. pindolol;
(y) Antiarteriosclerotic agents, e.g. clofibrate, pentoxifylline;
(z) Drugs for treatment of ulcers, e.g. cimetridine, ranitidine;

Other, e.g. nicotine.

It will be appreciated that the drug may be added to the present composition not only in its free form, but also as a simple pharmacologically acceptable derivative, such as an ether, an ester, an amide, an acetal, a salt and the like. In some cases, such derivatives may actually be preferred.

Particularly preferred drugs for use in the present composition are morphine, nifedipine, phenazocine, verapamil and saltutamol.

These drugs can be used either singly or as a mixture of two or more. The amount of drug to be blended in a solid dosage unit will generally be enough to maintain a therapeutic level of the drug in the bloodstream for a predetermined period.

In addition to the constituents discussed above, the present pharmaceutical composition may also contain certain of the known excipients, such as lubricants, binders, vehicles, coloring agents, taste controlling agents and odor controlling agents, that are employed to improve the appearance, odor or taste of pharmaceutical preparations.

In a particularly preferred embodiment of the present composition, the granules contain between 2% and 15% (w/w), especially between 4% and 10% (w/w), of a binder to improve the binding and strength of the dosage form. Suitable binders include starch, dextrin, tragacanth, gelatin, polyvinylpyrrolidone, polyvinylalcohol or, which is especially preferred, a mucosa adhesive cellulose such as a carboxyalkyl cellulose or a hydroxyalkyl cellulose especially sodium carboxymethyl cellulose, hydroxypropylmethyl cellulose or, most especially, hydroxypropyl cellulose. Compositions according to this invention having both extragranular adhesive cellulose and intragranular adhesive cellulose (as binder) have been found to exhibit particularly good qualities of adhesion and strength.

It should be noted that when the same cellulosic material is used in the present composition as the water soluble hydroxyalkyl cellulose, the extragranular mucosa-adhesive cellulose and the binder, then the amount of cellulosic material present in each dosage form is at least the sum of that added as water-soluble hydroxyalkyl cellulose and that added as binder and extragranular adhesive.

The present composition is prepared by compressing mucosa-adhesive cellulose coated granules of a mixture of a drug, a higher aliphatic alcohol and a hydrated water soluble hydroxyalkyl cellulose.

The mucosa-adhesive cellulose coated granules may be prepared in a number of ways. For example, the drug may first be incorporated in the higher alcohol or the cellulosic material prior to blending this with the remainder of the granules' constituents. Alternatively, and preferably, the drug may first be mixed with both the water soluble hydroxyalkyl cellulose and a binder before this mixture is blended with the higher alcohol.

The hydration of the water soluble hydroxyalkyl cellulose is effected at any convenient stage during the mixing of the granules' ingredients. It must be carried out carefully since excessive hydration of the hydroxyalkyl cellulose results in an unmanageable granular mass, whilst insufficient hydration results in a erratic and inferior release rate of medicament from the final composition. The degree of hydration is in practice preferably that obtained by the addition of a quantity of water between 1 and 5, especially, 2 and 3 times, the dry weight of the water soluble hydroxyalkyl cellulose.

Once the granules' ingredients have been mixed and hydrated they are then granulated and sieved to afford granules of a suitable granule size, preferably less than 100, μm. Finally the granules are mixed with extra-granular mucosa-adhesive cellulose to form mucosa-adhesive cellulose coated granules.

It is important to note that the above methods and processes of granule formation are merely illustrative. Other preparations of the present mucosa-adhesive coated granules will be immediately apparent to those skilled in this art.

The compressed granules may be formed into any suitable oral dosage form by the use of, for example, a punch, die or press. In order to facilitate the use of the present composition in the mucosal, especially buccal, administration of drugs, however, there is provided, in a further aspect of the present invention, a kidney-shaped oral vehicle adapted to fit closely the shape of the buccal cavity. Such an oral vehicle may be prepared using kidney shaped punches and dies.

Oral dosage units according to the present invention in the form of kidney-shaped oral vehicles have been found to be particularly convenient in the mucosal, especially buccal, administration of the drugs. It has been found that most patients may eat and drink freely whilst the kidney shaped oral vehicle is in position.

BRIEF DESCRIPTION OF THE DRAWINGS

The present invention will now be described in greater detail, with reference to certain exemplary embodiments as set forth in the examples and illustrated in the drawings, to which the present invention is not intended to be confined. In the drawings.

DESCRIPTION OF THE PREFERRED EMBODIMENTS

Figure 1A:
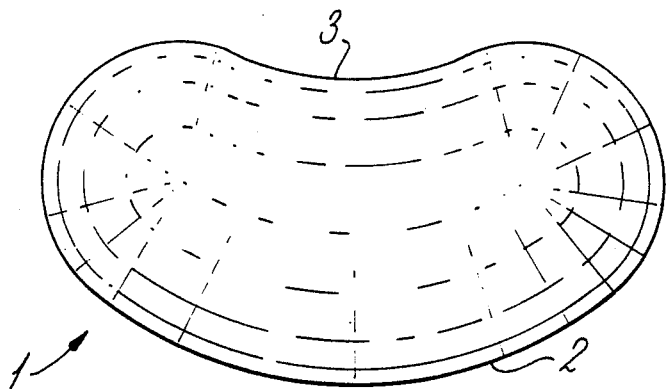
FIG. 1A is a plan view of a preferred kidney-shaped tablet in accordance with the present invention.
Figure 1B:
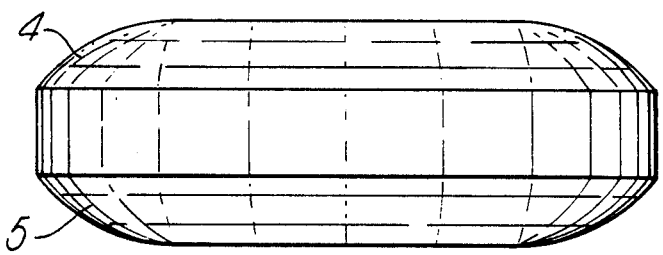
FIG. 1B is a side elevation view thereof.
Figure 1C:
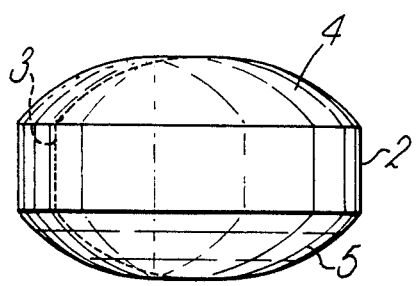
FIG. 1C is a rear elevation view thereof.

In the following examples referring to FIG. 1A, a kidney-shaped oral tablet 1 is shown having a convex side 2 and a concave side 3. As seen in FIGS. 1B and 1C, both the upper portion 4 and the lower portion 5 of the body are round. In use, this kidney-shaped tablet is placed in the buccal cavity of a patient with the concave side 3 uppermost.

The following examples are given to further illustrate the present invention. The scope of the invention is not, however, meant to be limited to the specific details of the examples:

EXAMPLE 1

The following ingredients were used to prepare one thousand tablets (200 mg total weight, 10 mg of morphine sulphate).

| Ingredients | % | Weight (gm) |
| --- | --- | --- |
| Morphine Sulphate | 7.5 | 10.0 |
| Mannitol | 25.0 | 50.0 |
| Lactose (Anhydrous) | 15.0 | 35.0 |
| Hydroxyethyl cellulose (Natrosol 250 HX) | 13.3 | 26.6 |
| Hydroxypropyl cellulose (Klucel HF) | 12.5 | 25.0 |
| Cetostearyl Alcohol | 26.7 | 53.4 |
| Water | q.s. | q.s. (approx. 65 g.) |

The morphine sulphate, mannitol, lactose, hydroxyethyl cellulose and hydroxypropyl cellulose (15 g., added as a binder) were dry blended until thoroughly mixed. The mixture was then hydrated (approx. 65 g.) until a wet granular mass was obtained. The hydrated material was then partially dried in a Fluid Bed Dryer (FBD) at 60° C., granulated and sieved through a 12 mesh screen. The granulated material was then completely dried in the FBD at 60° C., regranulated and sieved through a 16 mesh screen.

To the warmed morphine sulphate-containing granules was added molten cetostearyl alcohol and the whole was mixed thoroughly. The mixture was allowed to cool in the air, regranulated and sieved through a 16 mesh screen.

The extragranular hydroxypropyl cellulose (10 g.) was then added and mixed with the granules, until at least a substantial proportion of the granules had a coating of hydroxyproply cellulose.

Finally the coated granules were compressed and formed, using a kidney-shaped punch, into kidney-shaped tablets. This process afforded one thousand 200 mg. tablets, each containing 10 mg. of morphine sulphate.

EXAMPLE 2

The method of Example 1 was followed except that the amount of morphine sulphate employed was increased to 20 g. and the amount of lactose employed was reduced to 25 g.

EXAMPLE 3

The method of Example 1 was followed except that the amountof morphine sulphate employed was increased to 30 g. and the amount of lactose employed was decreased to 15 g.

EXAMPLE 4

The method of Example 1 was followed except that sodium carboxymethyl cellulose replaced hydroxypropyl cellulose as the mucosa adhesive cellulose and binder.

EXAMPLE 5

The method of Example 1 was followed except that morphine sulphate was replaced by nitroglycerin (5 g.), added as a 1 in 10 blend of nitroglycerin and lactose, the amount of anhydrous lactose being reduced to zero.

EXAMPLE 6

The following ingredients were used to prepare one thousand tablets (200 mg. total weight, 20 mg. nifedipine).

| Ingredients | % | Weight (gm) |
| --- | --- | --- |
| Nifedipine (micronised) | 10 | 20 |

| Ingredients | % | Weight (gm) |
|---|---|---|
| Xylitol | 25 | 50 |
| Anhydrous Lactose | 42.75 | 85.5 |
| Hydroxyethyl cellulose (Natrosol 250HX) | 3.25 | 6.5 |
| Hydroxypropyl cellulose (Klucel HF) | 10 | 20 |
| Sodium carboxymethyl cellulose (Blanose 7MFD) | 2.5 | 5 |
| Cetostearyl alcohol | 6.5 | 13 |
| Water | | 25 |

The nifedipine, xylitol, lactose, hydroxyethyl cellulose and hydroxypropyl cellulose (15 g., added as a binder) were dry blended until thoroughly mixed. The mixture was then hydrated (approx. 25 ml.) until a wet granular mass was obtained. The hydrated material was then partially dried in a Fluid Bed Dryer (FBD) at 60° C., granulated and sieved through a 12 mesh screen. The granulated material was then completely dried in the FBD at 60° C., regranulated and sieved through a 16 mesh screen.

To the warmed nifedipine containing granules was added molten cetostearyl alcohol and the whole was mixed thoroughly. This mixture was allowed to cool in the air, regranulated and sieved through a 16 mesh screen.

The extragranular hydroxypropyl cellulose (5 g) and sodium carboxymethyl cellulose (5 g) was then added and mixed with the granules, until at least a substantial proportion of the granules had a coating of hydroxypropyl cellulose. Finally the coated granules were compressed and formed, using a kidney-shaped punch, into kidney-shaped tablets.

This process afforded one thousand 200 mg. tablets, each containing 20 mg. of nifedipine.

EXAMPLE 7

The method of Example 6 was repeated with the following ingredients,

| Ingredients | % | Weight (g.) |
|---|---|---|
| Buprenorphine | 0.25 | 0.5 |
| Anhydrous Lactose | 24.75 | 49.5 |
| Hydroxyethyl cellulose (Natrosol 250 HX) | 12.5 | 25 |
| Cetostearyl alcohol | 25 | 50 |
| Xylitol | 25 | 50 |
| Hydroxypropyl cellulose (intragranular) (klucel HF) | 7.5 | 15 |
| Hydroxypropyl cellulose (extragranular) | 2.5 | 5 |
| Sodium carboxymethyl cellulose (extragranular) (Blanose 7MFD) | 2.5 | 5 |
| Water | | 60 |

This process afforded one thousand 200 mg. tablets, each containing 0.5 mg. of buprenorphine.

EXAMPLE 8

The method of Example 6 was repeated with the following ingredients,

| Ingredient | % | Weight (g) |
|---|---|---|
| Phenazocine hydrobromide | 5 | 10 |
| Anhydrous Lactose | 10 | 20 |
| Hydroxyethyl cellulose (Natrosol 250 HX) | 15 | 30 |
| Cetostearyl alcohol | 30 | 60 |
| Mannitol | 27.5 | 55 |
| Hydroxypropyl cellulose (intragranular) (klucel HF) | 7.5 | 15 |
| Hydroxypropyl cellulose (extragranular) | 5 | 10 |
| Water | | 70 |

CLINICAL TRIALS

Figure 2:
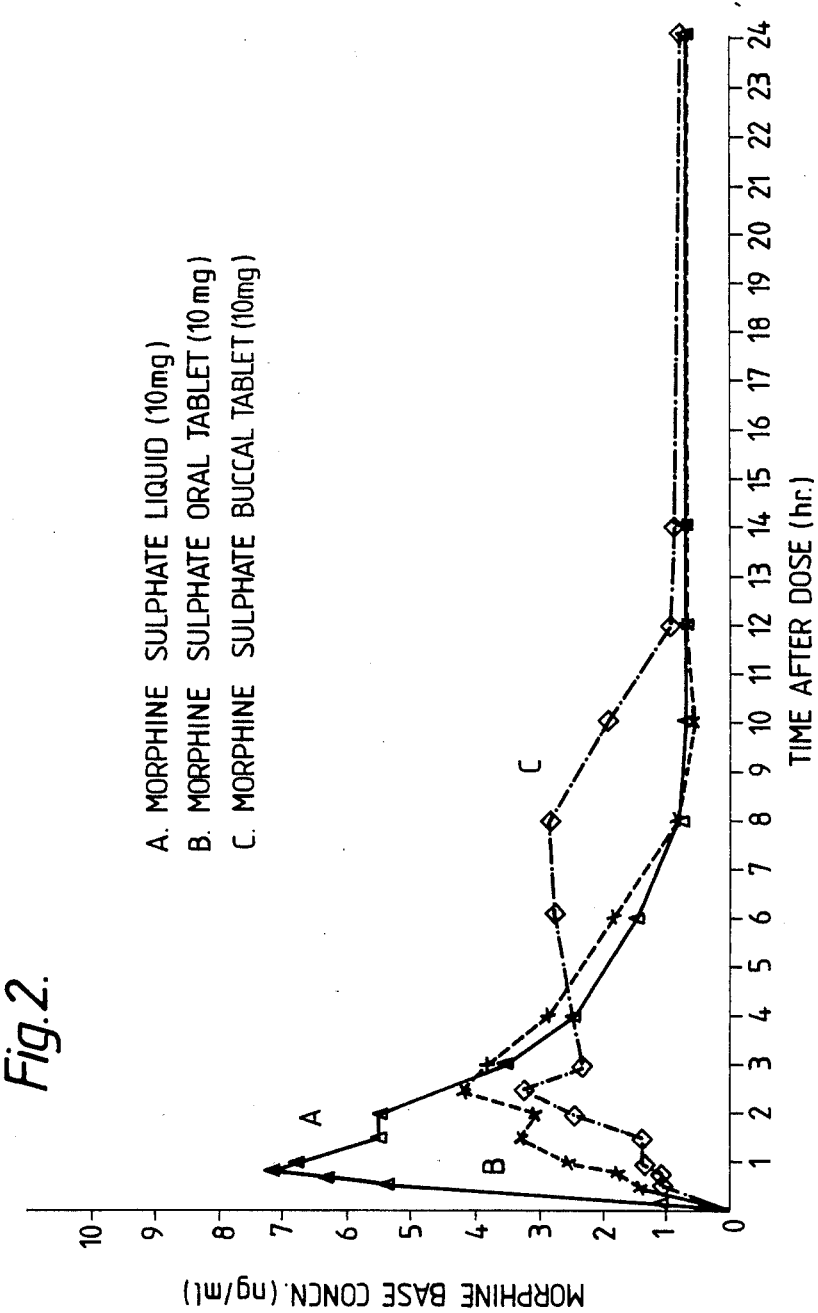
FIG. 2 is a graphic representation showing the morphine plasma level achieved, as a function of time, by four patients using three morphine sulphate formulation.

A comparative single dose pharmacokinetic study of three morphine sulphate preparations, namely morphine sulphate 10 mg. buccal tablets (prepared as described in Example 1), morphine sulphate liquid 10 mg, and a sustained release morphine sulphate oral tablet 10 mg (orally administered MST CONTINUS tablet) was conducted using four patients for each preparation. Morphine levels in plasma were determined using a liquid-solid extraction followed by radio immuno-assay. The results are given in FIG. 2.

From this Figure it can be seen that the bioavailability of morphine sulphate is significantly prolonged using the present buccal tablets, compared with the bioavailability achieved by either a liquid morphine formulation or an orally administered sustained release morphine formulation.

Figure 3:
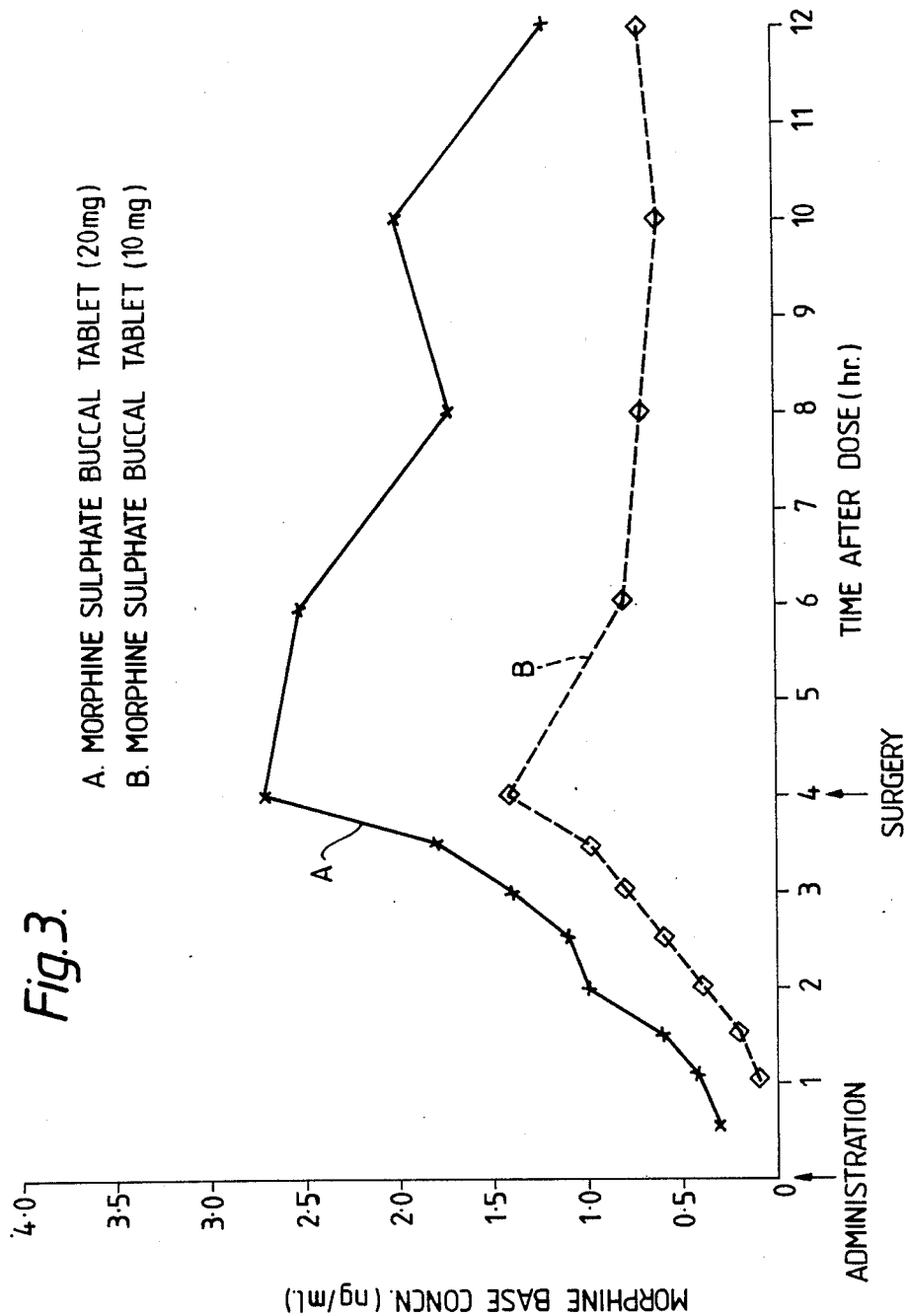
FIG. 3 is a graphic representation showing the morphine plasma levels achieved as a function of time by nine patients using a buccal morphine tablet prior to surgery.

A single dose pharmacokinetic study of morphine sulphate buccal tablets, 10 mg and 20 mg, was conducted using nine patients. The tablet was placed in position in the buccal cavity four hours prior to laparoscopy. Morphine levels in plasma were determined using an LSE/RIA method. Results are given in FIG. 3. Again the prolonged nature of the morphine sulphate bioavailability is apparent from this Figure.

PRODUCT ADHERENCE TO MUCOSA

Placebo tablets, prepared as described in Example 1, but with morphine sulphate replaced by lactose (10.0 gm) were used to determine the adherence of tablets, prepared according to this invention, to the oral mucosa.

The trial was carried out using nine volunteers. One tablet was put in place in the buccal cavity twice daily (at 12 hour intervals), using both sides of the mouth alternately, over a seven day period.

Subjects were asked to record the duration of each tablet in the buccal cavity. Results are given in the Table.

TABLE

| | Tablet Duration (hr) | |
|---|---|---|
| Subject | Night | Day |
| 1 | 12 | 9.7 |
| 2 | 12 | 8.0 |
| 3 | 12 | 7.2 |
| 4 | 12 | 5.9 |
| 5 | 12 | 11.0 |
| 6 | 12 | 8.5 |
| 7 | 12 | 10.9 |
| 8 | 12 | 8.6 |
| 9 | 12 | Subject found tablets unacceptable |
| Average | 12 | 8.4 |

While the invention has been described with respect to particular compositions, it is apparent that variations and modifications of the invention can be made without departing from the spur of scope thereof.

What is claimed is:

1. Arrangement adapted for application and adherence to the mucosa of the oral or nasal cavity for sustained release there of an orally administerable drug, said arrangement comprising a body having an orally administerable drug distributed therein and having a size and shape suitable for insertion into and retention in the oral or nasal cavity, said body being formed of granules of a higher aliphatic alcohol of 8-18 carbon atoms and a hydrated water soluble hydroxyloweralkyl cellulose having said drug distributed therethrough and being coated with a cellulose derivative which is adherent to the mucosa, whereby upon insertion into the oral or nasal cavity said body adheres to the mucosa thereof and the drug is there slowly released and absorbed.

2. Arrangement according to claim 1 wherein said cellulose derivative which is adherent to the mucosa is powdered.

3. Arrangement according to claim 1 wherein said cellulose derivative is a carboxyloweralkyl cellulose or a hydroxyloweralkyl cellulose.

4. Arrangement according to claim 1 wherein said cellulose derivative is sodium carboxymethyl cellulose, hydroxypropylmethyl cellulose or hydroxypropyl cellulose.

5. Arrangement according to claim 1 wherein said cellulose derivative is hydroxypropyl cellulose.

6. Arrangement according to claim 1 wherein the amount of said cellulose derivative coating is between about 2% and 15% by weight of the weight of said body.

7. Arrangement according to claim 1 wherein the amount of said cellulose derivative coating is between about 4% and 10% by weight of the weight of said body.

8. Arrangement according to claim 1 wherein the higher aliphatic alcohol is cetyl alcohol or cetostearyl alcohol.

9. Arrangement according to claim 1 wherein the higher aliphatic alcohol comprises between 5% and 35% (w/w), of the total weight.

10. Arrangement according to claim 1 wherein the higher aliphatic alcohol comprises between 10% and 30% (w/w) of the total weight.

11. Arrangement according to claim 1 wherein the water soluble hydroxyalkyl cellulose is hydroxymethyl cellulose, hydroxyethyl cellulose, hydroxypropyl cellulose or hydroxypropylmethyl cellulose.

12. Arrangement according to claim 1 wherein the water soluble hydroxyalkyl cellulose is hydroxyethyl cellulose.

13. Arrangement accoding to claim 1 wherein the water soluble hydroxyalkyl cellulose comprises between 2% and 15% (w/w) of the total weight.

14. Arrangement according to claim 1 wherein the drug is morphine, nifedipine, phenazocine, verapamil or salbutamol.

15. Arrangement according to claim 1 wherein the drug is morphine.

16. Arrangement according to claim 1 wherein said body is in the form of a kidney-shaped tablet.

17. A process for the preparation of a sustained release, oral pharmaceutical composition in solid unit dosage form, the composition being adapted for application to the mucosa of the oral or nasal cavity, comprising forming granules comprising an orally administerable drug, a higher aliphatic alcohol of 8-18 carbon atoms and hydrated water soluble hydroxyloweralkyl cellulose, coating the granules with a cellulose derivative which is adherent to the mucosa, and compressing the mucosa adhesive cellulose coated granules to give a solid unit dosage form.

18. A process according to claim 17 wherein the graunules are formed by a process comprising mixing the drug and the water soluble hydroxyloweralkyl cellulose to form a drug-containing mixture, hydrating the drug-containing mixture to form a wet granular mass, drying the wet granular mass to form a dry granular mass, and mixing the dry granular mass with a higher aliphatic alcohol of 8-18 carbon atoms.

* * * * *